(12) United States Patent
Marka et al.

(10) Patent No.: US 10,274,577 B2
(45) Date of Patent: Apr. 30, 2019

(54) MEDICAL DEVICE SYSTEM AND A METHOD FOR LOCATING MEDICAL DEVICES AND MOBILE CONTROL UNITS OF SAID MEDICAL DEVICE SYSTEM

(71) Applicant: TRUMPF MEDIZIN SYSTEME GMBH + CO. KG, Saalfeld (DE)

(72) Inventors: Rudolf Marka, Ismaning (DE); Serhan Özhan, Munich (DE); Gel Han, Munich (DE)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 0 days.

(21) Appl. No.: 15/322,318

(22) PCT Filed: Jun. 26, 2015

(86) PCT No.: PCT/EP2015/064541
§ 371 (c)(1),
(2) Date: Dec. 27, 2016

(87) PCT Pub. No.: WO2016/001087
PCT Pub. Date: Jan. 7, 2016

(65) Prior Publication Data
US 2017/0123043 A1    May 4, 2017

(30) Foreign Application Priority Data
Jun. 30, 2014   (DE) .................. 10 2014 212 650

(51) Int. Cl.
*G01S 5/02* (2010.01)
*H04W 4/80* (2018.01)
(Continued)

(52) U.S. Cl.
CPC ............ *G01S 5/0252* (2013.01); *A61B 90/98* (2016.02); *G01S 5/0268* (2013.01);
(Continued)

(58) Field of Classification Search
None
See application file for complete search history.

(56) References Cited

U.S. PATENT DOCUMENTS 9,250,310 B2 *   2/2016   Hasegawa .................. G01S 5/02
2003/0043073 A1 *  3/2003   Gray ...................... G01S 5/0215
                                                        342/465

(Continued)

FOREIGN PATENT DOCUMENTS

DE      2001035531     10/2006
DE      2009021783      9/2010
DE      2010040594      3/2012

OTHER PUBLICATIONS

English translation of the PCT Search Report and Written Opinion for PCT/EP2015/064541, completed Sep. 15, 2015.
(Continued)

*Primary Examiner* — Charles N Appiah
*Assistant Examiner* — Frank E Donado
(74) *Attorney, Agent, or Firm* — Barnes & Thornburg LLP

(57) ABSTRACT

A medical apparatus system is provided, the medical apparatus system comprising: at least one medical apparatus (2), at least one mobile control unit (3), for a medical apparatus (2), having a WLAN transmitting module (4) and a further radio transmitting module (5), at least one WLAN access point (6) having at least one antenna, at least one further radio reading module (7), and control device (8) connected to the at least one WLAN access point (7) and the at least one further radio reading module (7) in order to locate the medical apparatus and/or the mobile control unit in a process reliable manner.

19 Claims, 2 Drawing Sheets

(51) Int. Cl.
*A61B 90/98* (2016.01)
*H04M 11/00* (2006.01)
*H04W 88/10* (2009.01)
*H04W 4/04* (2009.01)
*A61B 34/20* (2016.01)

(52) U.S. Cl.
CPC ......... H04M 11/007 (2013.01); H04W 4/043 (2013.01); H04W 4/80 (2018.02); *A61B 2034/2051* (2016.02); *A61B 2034/2072* (2016.02); *G01S 5/0257* (2013.01); *H04W 88/10* (2013.01)

(56) References Cited

U.S. PATENT DOCUMENTS

| | | | |
|---|---|---|---|
| 2005/0085257 A1* | 4/2005 | Laird | A61B 5/04 455/550.1 |
| 2005/0181804 A1 | 8/2005 | Misikangas et al. | |
| 2007/0184850 A1 | 8/2007 | Hupp et al. | |
| 2008/0204322 A1 | 8/2008 | Oswald et al. | |
| 2010/0277309 A1* | 11/2010 | Anderson | A61B 5/1113 340/539.13 |
| 2013/0035109 A1* | 2/2013 | Tsruya | G01S 5/0252 455/456.1 |
| 2013/0053056 A1 | 2/2013 | Aggarwal et al. | |
| 2013/0143595 A1* | 6/2013 | Moshfeghi | H04W 4/029 455/456.1 |
| 2013/0308685 A1 | 11/2013 | Nagai | |
| 2013/0337842 A1* | 12/2013 | Wang | A61B 5/0024 455/456.4 |
| 2014/0087752 A1 | 3/2014 | Zhu et al. | |
| 2014/0335823 A1* | 11/2014 | Heredia | H04L 51/38 455/411 |
| 2014/0344758 A1* | 11/2014 | Kozakura | G06F 17/30274 715/835 |
| 2015/0290060 A9* | 10/2015 | Hayes | A61G 7/018 5/600 |

OTHER PUBLICATIONS

English translation of the International Preliminary Report on Patentability for PCT/EP2015/064538, completed Jan. 12, 2017.

* cited by examiner

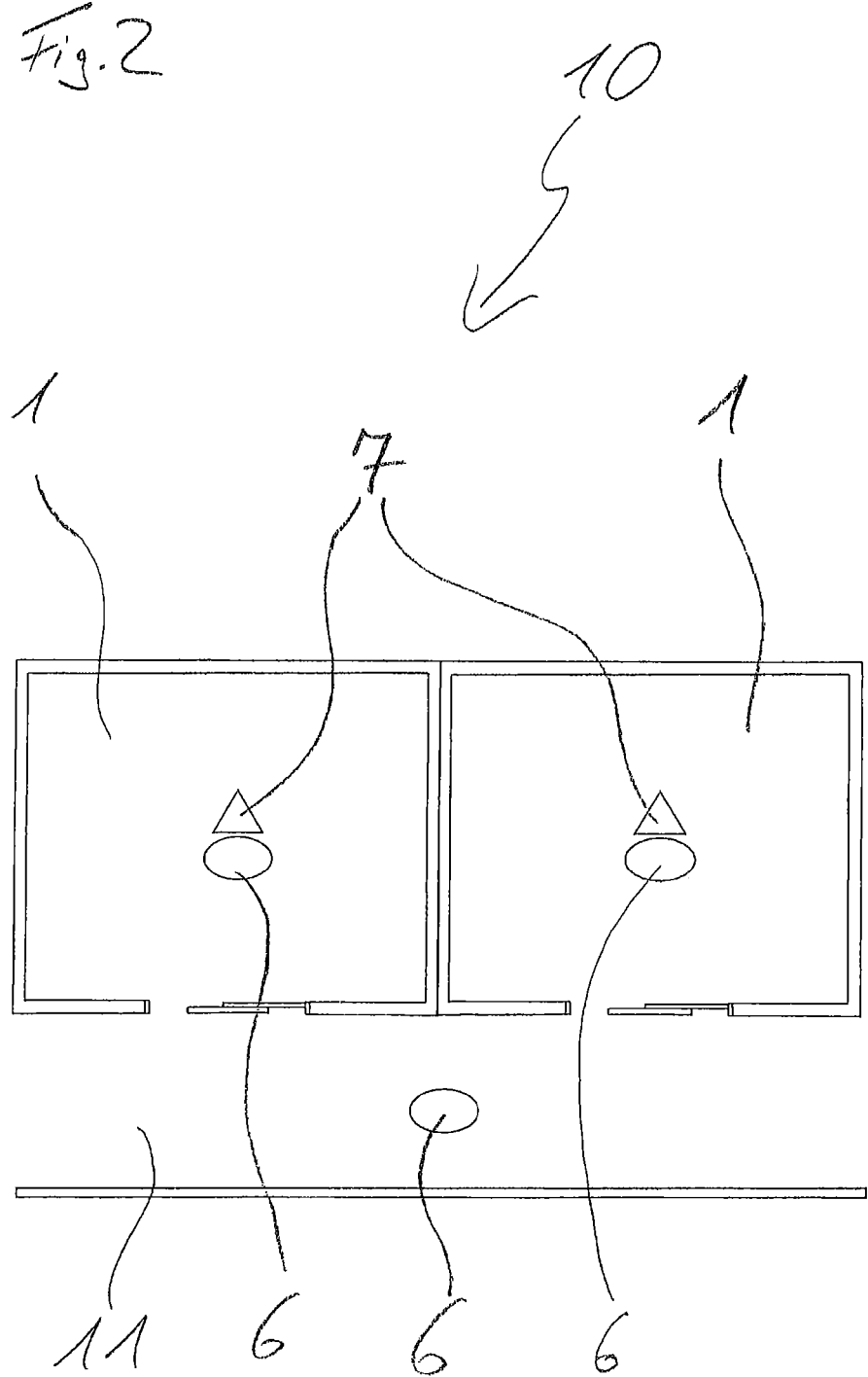

MEDICAL DEVICE SYSTEM AND A METHOD FOR LOCATING MEDICAL DEVICES AND MOBILE CONTROL UNITS OF SAID MEDICAL DEVICE SYSTEM

CROSS REFERENCES TO RELATED APPLICATIONS

This application is a U.S. national phase of PCT/EP2015/064541, filed on Jun. 26, 2015, which claims the benefit of and priority to German Patent Application Serial No. 102014212650.9, filed on Jun. 30, 2014, both of which are incorporated herein by this reference in their entirety.

The invention relates to a medical apparatus system and a method for locating medical apparatuses and/or mobile control units of the medical apparatus system, in particular to a system and a method by which a presence of the medical apparatus and its control unit in a room of a section of a building can surely be determined.

Up to now, mobile control units of medical apparatuses are located and localized e.g. via infrared signals ensuring that the control unit and the medical apparatus are in visual contact. Further options for locating mobile control units are the use of a single radio service or an distance identification via e.g. 3D sensors.

However, thereby, the problem arises that a sure locating is not possible or the position is to detect very imprecisely.

Therefore, the object to provide a medical apparatus system and a method for locating medical apparatuses and mobile control units not comprising the above disadvantages and enabling a process reliable exact locating is underlying the invention.

The object is achieved by a medical apparatus system according to claim 1 and a method according to claim 13. Further developments of the invention are subject-matter of the subclaims.

By the medical apparatus system and method according to the invention, it is possible to ensure an exact, process reliable locating of medical apparatuses and/or mobile control units by means of two different detection principles.

The invention is now elucidated by means of embodiments referring to the attached drawings.

In particular:

FIG. 2 shows a floor plan of a section of a building with operating theaters.

Figure 1:
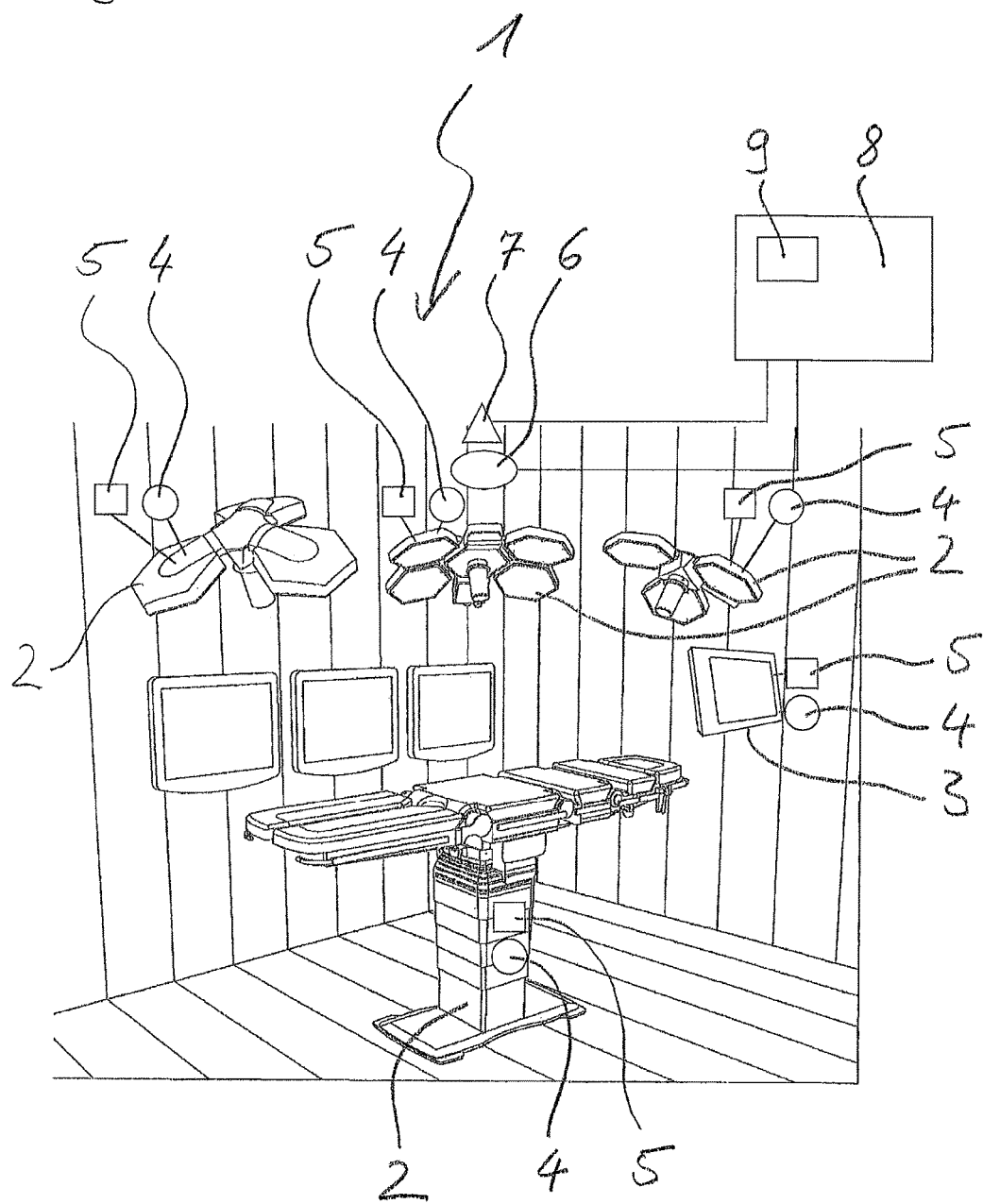
FIG. 1 shows a perspective view of an operating theater.

In FIG. 1, a perspective view of an operating theater as room 1 in a section of a building, e.g. in a hospital, is shown. In the room 1, a surgical table and several surgical lamps as medical apparatuses 2 are illustrated. Further, a tablet PC is provided as a mobile control unit 3 for controlling at least one of the medical apparatuses 2, wherein a medical apparatus control system is formed then. Depending on whether the medical apparatuses 2 and/or the mobile control unit 3 shall be located, the medical apparatuses 2 and the mobile control unit 3 are respectively optionally equipped with a WLAN transmitting module 4 and a further radio transmitting module 5.

In the room 1, furthermore, a WLAN access point 6 and a further radio reading module 7 are provided. If several such rooms 1 are provided, each room is provided with a WLAN access point 6 and a further radio reading module 7. In a case in which a signal transmission through walls of the rooms 1 is possible, alternatively, a single WLAN access point 6 and a single further radio reading module 7 are provided for several rooms. The WLAN access point 6 and the further radio reading module 7 are connected to a control device 8.

These components, the WLAN transmitting modules 4, the further radio transmitting modules 5, the WLAN access points 6, the further radio reading modules 7 and the control device 8, are constituents of a medical apparatus system.

In this embodiment, a single mobile control unit 3 and four medical apparatuses 2, namely, the surgical table and three surgical lamps, are illustrated. In alternative embodiments, also several mobile control units 3 and/or another quantity of medical apparatuses 2 can be provided.

The WLAN access point 6 is provided with at least one antenna, in particular, a smart antenna. The smart antenna can determine the direction from which a query of an apparatus comes via WLAN and, thereupon, it transmits or receives data from this direction or in this direction in a targeted manner. Thereby, there are less overlaps and deteriorations upon a use of multiple apparatuses and a higher data throughput is possible. The WLAN access point 6 works in a 5 GHz band. Alternatively, he works in two different frequency bands, namely the 2.4 GHz band and the 5 GHz band or in a combination of the 2.4 GHz band and the 5 GHz band in order to avoid potential deteriorations in a specific band.

The WLAN transmitting modules 4 of the medical apparatuses 2 and the mobile control unit 3 are provided with a respective address and transmit signals in the corresponding frequency band of the WLAN access point 6.

By the WLAN access point 6, a signal strength of the signals transmitted by the WLAN transmitting modules 4 is detected and assigned to the respective WLAN transmitting module 4 by the received address.

In this embodiment, the further transmitting modules 5 of the medical apparatuses 2 and the mobile control unit 3 as well as the further radio reading modules 7 are "Bluetooth Low Energy" (BLE) modules. In an alternative embodiment, the radio transmitting modules and reading modules are e.g. RFID modules.

The control device 8 is provided with a memory area 9 where data sets of later elucidated signal strength combinations, so-called "fingerprints", can be stored.

In FIG. 2, a map of a floor plan of a section of a building 10 is shown. In the section of the building 10, two rooms 1, here the operating theaters, are illustrated. Outside the rooms, a corridor 11 extends.

In FIG. 2, it is to be seen that one of the WLAN access points 6 is located in each of the rooms 1. Also on the corridor 11, one of the WLAN access points 6 is provided. In the rooms 1, one of the further radio reading modules 7 is further respectively arranged.

In use, a locating of the medical apparatuses 2 and the control unit 3 is performed by the detection of the signal strengths by the WLAN device and by the further radio device.

For the detection by the WLAN device, data sets for several positions are stored in the memory area 9 of the control device 8 in advance. Thereto, the respective data sets ("finger prints") of the respective signal strengths at the individual WLAN access points 6 are uniquely stored for the several positions in the memory area 9 e.g. by a laptop having an additional omni-directional antenna.

Further, an image of a map with the floor plan of the section of the building to be detected is also stored in the memory area 9.

The signal strengths of the signals transmitted by the WLAN transmitting modules 4 assigned to the medical apparatuses 2 or to the mobile control unit 3 via the respective address are detected by the three WLAN access points. Alternatively, the detection is also possible by more or less WLAN access points 6.

Via a selected algorithm, the signal strengths are then compared with the "finger prints" and, by means of the map, it is calculated, i.e. detected, in which of the rooms 1, the medical apparatus 2 and/or the mobile control unit 3 are located. The room 1 where the mobile control unit 3 is located is then known if the current received signal strengths of the at least three access points 6 in the memory area 9 are located in the analog or the almost analog combination. Moreover, it can be concluded to the position in X and Y where the (almost) similar combination has already been measured upon storing the finger prints.

The BLE are located by the signal strengths of the signals, transmitted by the further radio transmitting modules 7, detected by the further radio reading modules 7. In the rooms 1, a BLE reading module 7 is respectively installed at the ceiling. The BLE reading module 7 does not have to be mandatorily mounted at the ceiling, but it should be located centrally in the room. The receiving sensitivity of the BLE reading modules 7 is reduced such that an evident distinction of the detected signal strengths coming out of the different rooms is possible. The receiving sensitivity should be adjusted such that signals from outside the room 1 where the respective BLE reading module 7 is located are not detected or preferably with minimum signal strength. By means of a defined minimum signal strength, it is then determined in which room the medical apparatus 2 or the mobile control unit 3 is located. In this embodiment, exactly one BLE reading module 7 is assigned to each room. In alternative embodiments, also several or no BLE reading module 7 can be assigned to each room. The determination in which room 1 the medical apparatus 2 or the mobile control unit 3 is located is performed by the control device 8.

As soon as the mobile control unit 3 or one of the medical apparatuses 2 is switched on, signals, the signal strengths of which are detected at the three WLAN access points 6 and transmitted to the control device 8 for determining the position, are transmitted by the WLAN transmitting module 4. Simultaneously, signals are transmitted by the further radio transmitting module 5 and the BLE reading modules 7 receive the signal of the further radio transmitting module 5. Optionally, WLAN and Bluetooth signals are continuously transmitted from the medical apparatuses 2, whereas, in the mobile control unit 3, Bluetooth signals are always transmitted and WLAN signals only when the mobile control unit 3 is switched on. In alternative embodiments, the signals of the WLAN transmitting module 4 and the further radio transmitting module 5 are not simultaneously but e.g. sequentially, as the case may be, cyclically, transmitted and/or received. The determinations of the current position via the WLAN signal strengths and of the current room via the BLE locating are superimposed and, as a result, an unambiguous determination of the room 1 where the medical apparatus 2 or the mobile control unit is located is enabled.

The individual embodiments can be combined with one another.

What is claimed is:

1. A medical apparatus system, comprising
at least one medical apparatus having a WLAN transmitting module and a further radio transmitting module and at least one mobile control unit, for a medical apparatus, having a WLAN transmitting module and a further radio transmitting module, at least one WLAN access point having at least one antenna, at least one further radio reading module, and a control device connected to the at least one WLAN access point to determine a WLAN position of the at least one medical apparatus and the at least one mobile control unit based on a signal from the WLAN transmitting module of the respective at least one of the medical apparatus or the mobile control unit, the control device also connected to the at least one further radio reading module to determine a radio position of the at least one medical apparatus and the at least one mobile control unit based on a signal from the further radio transmitting module of the respective at least one of the medical apparatus or the mobile control unit, the control device determining a position of the at least one medical apparatus and the at least one mobile control unit by superimposing the radio position on the WLAN position.

2. The medical apparatus system of claim 1, wherein the at least one WLAN access point comprises transmitting and receiving devices for different frequencies.

3. The medical apparatus system of claim 2, wherein at least three WLAN access points are provided.

4. The medical apparatus system of claim 3, wherein the WLAN access points are configured to detect a strength of a signal of the at least one WLAN transmitting module of the respective at least one of the medical apparatus or the mobile control unit.

5. The medical apparatus system of claim 4, wherein the control device comprises a memory area for data sets of signal strength combinations for individual positions of the at least one medical apparatus and of the at least one mobile control unit.

6. The medical apparatus system of claim 5, wherein the control device comprises a memory area for data sets of a map including a floor plan of an area in which the signal strength combinations are detected.

7. The medical apparatus system of claim 6, wherein the detected area comprises rooms in a section of a building and an area outside the rooms, and an individual WLAN access point is respectively provided in the rooms and an individual WLAN access point is provided in the area outside the room, and the control device is configured to determine on the basis of the stored data sets whether a currently detected position of the at least one medical apparatus or of the at least one mobile control unit is located inside or outside of one of the rooms and in which room.

8. The medical apparatus system of claim 1, wherein the at least one further radio reading module is configured to detect a strength of a signal of the at least one further radio transmitting module of the respective at least one of the medical apparatus or the mobile control unit.

9. The medical apparatus system of claim 8, wherein an individual further radio reading module is provided in a room, and wherein the medical apparatus system is configured to determine via the strength of the signal whether the at least one further radio transmitting module of the respective at least one of the medical apparatus or the mobile control unit is located inside or outside of the room.

10. The medical apparatus system of claim 1, wherein the further radio transmitting module of the respective least one of the medical apparatus or the mobile control unit is a Bluetooth Low Energy transmitting module and the further radio reading module is a Bluetooth Low Energy reading module.

11. The medical apparatus system of claim 1, wherein the further radio transmitting module of the respective at least one of the medical apparatus or the mobile control unit and the further radio reading module are RFID modules.

12. A medical apparatus control system with a medical apparatus system according to claim 1, wherein the at least one medical apparatus can be actuated by the mobile control unit.

13. The medical apparatus system of claim 1, wherein the WLAN position and the radio position are determined simultaneously.

14. A method for locating medical apparatuses and mobile control units comprises
  determining a signal strength of a detected signal of at least one WLAN transmitting module of a respective medical apparatus or mobile control unit via a WLAN access point to determine a WLAN position of the medical apparatus and mobile control unit,
  determining a signal strength of a detected signal of at least one further radio transmitting module via a further radio reading module of a respective medical apparatus or mobile control unit to determine a radio position of the medical apparatus and mobile control unit, and
  determining a position of the medical apparatus and of the mobile control unit by superimposing the radio position on the WLAN position.

15. The method of claim 14, wherein the signal strength of the WLAN transmitting module of the respective at least one of the medical apparatus or the mobile control unit and of the further radio transmitting module of the respective at least one of the medical apparatus or the mobile control unit are determined simultaneously.

16. The method of claim 14, wherein the position is determined by several WLAN access points and by a further radio reading module assigned to a room of a section of a building.

17. The method of claim 14, wherein an actuation function of a mobile control unit for the medical apparatus to be actuated is deactivated if it is determined that the mobile control unit is not in the same room of a section of a building as the medical apparatus to be controlled.

18. The method of claim 14 with a medical apparatus system, wherein the signal strength combinations of the individual positions are determined by a detection device in advance.

19. The method of claim 14, further comprising determining the WLAN position and the radio position simultaneously.

* * * * *